United States Patent
Neff

(10) Patent No.: US 10,716,958 B2
(45) Date of Patent: Jul. 21, 2020

(54) METHOD FOR OPERATING A MEDICAL ROBOT, A MEDICAL ROBOT, AND A MEDICAL WORKSTATION

(75) Inventor: Thomas Neff, Munich (DE)

(73) Assignee: KUKA Deutschland GmbH, Augsburg (DE)

( * ) Notice: Subject to any disclaimer, the term of this patent is extended or adjusted under 35 U.S.C. 154(b) by 1226 days.

(21) Appl. No.: 13/170,690

(22) Filed: Jun. 28, 2011

(65) Prior Publication Data

US 2012/0022552 A1  Jan. 26, 2012

(30) Foreign Application Priority Data

Jul. 26, 2010 (DE) .................. 10 2010 038 427

(51) Int. Cl.
| | | |
|---|---|---|
| *A61N 7/02* | (2006.01) | |
| *A61B 34/30* | (2016.01) | |
| *A61N 7/00* | (2006.01) | |
| *A61B 17/00* | (2006.01) | |
| *A61B 34/20* | (2016.01) | |
| *A61B 90/00* | (2016.01) | |

(52) U.S. Cl.
CPC .............. *A61N 7/02* (2013.01); *A61B 34/30* (2016.02); *A61B 34/20* (2016.02); *A61B 2017/00699* (2013.01); *A61B 2034/2059* (2016.02); *A61B 2090/065* (2016.02); *A61B 2090/378* (2016.02); *A61N 2007/0091* (2013.01)

(58) Field of Classification Search
USPC ........................................................ 601/3
See application file for complete search history.

(56) References Cited

U.S. PATENT DOCUMENTS

| | | | |
|---|---|---|---|
| 6,128,522 A | 10/2000 | Acker et al. | |
| 6,425,865 B1 | 7/2002 | Salcudean et al. | |
| 2003/0144768 A1* | 7/2003 | Hennion et al. | 701/2 |
| 2005/0113691 A1* | 5/2005 | Liebschner | 600/437 |
| 2005/0154431 A1* | 7/2005 | Quistgaard et al. | 607/96 |
| 2006/0293598 A1* | 12/2006 | Fraser | A61B 8/08 600/439 |
| 2008/0021317 A1 | 1/2008 | Sumanaweera | |
| 2010/0041991 A1* | 2/2010 | Roundhill | 600/443 |
| 2012/0053597 A1* | 3/2012 | Anvari et al. | 606/130 |

FOREIGN PATENT DOCUMENTS

| | | |
|---|---|---|
| DE | 10 2007 046 700 A1 | 4/2009 |
| EP | 2070479 A1 | 6/2009 |

OTHER PUBLICATIONS

German Patent Office; Sesrch Report in German Patent Application No. 10 2010 038 427.5 dated Jun. 13, 2012; 5 pages.
European Patent Office; Search Report in European Patent Application No. 11173520.5 dated Nov. 17, 2011; 8 pages.

* cited by examiner

*Primary Examiner* — Jonathan Cwern
(74) *Attorney, Agent, or Firm* — Dorton & Willis, LLP

(57) ABSTRACT

A method for operating a medical robot, a medical robot, and a medical work station.
The invention relates to a method for operating a medical robot (2). The robot (2) includes a robot arm (5) having a plurality of members (7), drives (15) provided for moving the members (7), and an attaching device (9). The robot (2) also has a control device (6) for activating the drives (15), and a sound generating device (3) attached to the attaching device (9), which is provided to apply sound to a living organism (10), in particular a high-intensity focused ultrasound.

14 Claims, 2 Drawing Sheets

METHOD FOR OPERATING A MEDICAL ROBOT, A MEDICAL ROBOT, AND A MEDICAL WORKSTATION

Figure 1:
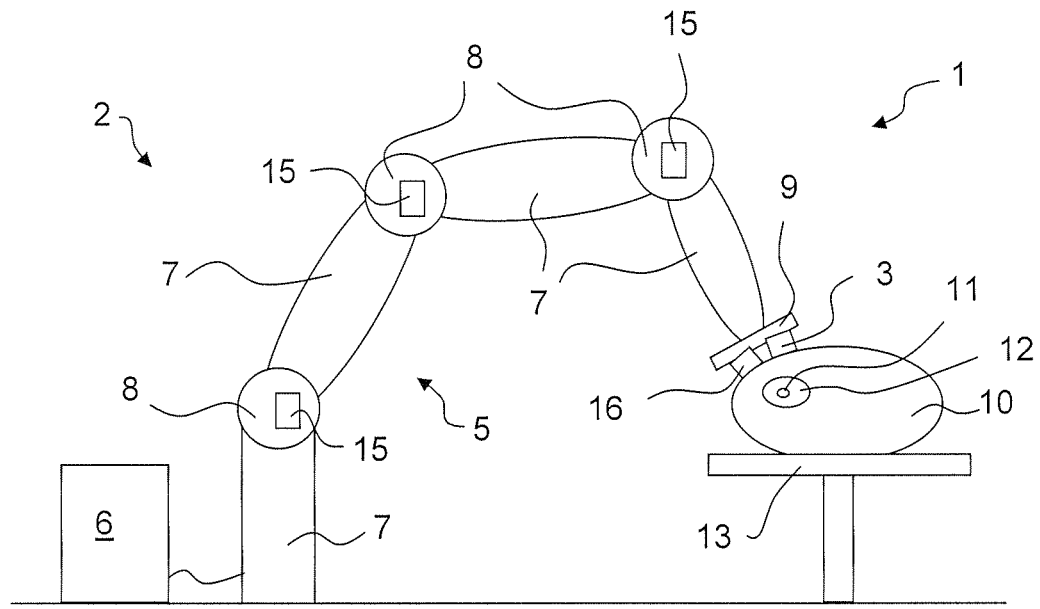

The invention relates to a method for operating a medical robot, a medical robot, and a medical work station.

Robots in general are manipulating machines, which are equipped with useful tools for automatic handling of objects, and are programmable in a plurality of motion axes, in particular with regard to orientation, position and process sequence. Robots usually have a robot arm with a plurality of members and programmable controllers (control devices), which control or regulate the motion sequences of the robot arm during operation.

For example, when treating tumors, so-called "high intensity focused ultrasound" (HIFU) may be employed to at least partially destroy tumor tissue. This involves a use of ultrasound in which tissue is heated and destroyed by a targeted sound bundle concentration.

The ultrasound is produced by appropriate sound generating devices, which, when operated as intended, are coupled with the skin of the living organism being treated, for example with the aid of a flow path of water or gel. If water is used as the flow path, then it should be degassified as completely as possible, since otherwise air bubbles could cause unwanted deflection and scattering of the sound.

US 2006/0293598 A1 discloses attaching the sound generating device for HIFU treatment to a robot arm, so that during the treatment the sound generating device follows a movement of the living organism being treated.

The object of the invention is to specify a method for operating a medical robot to which a sound generating device is attached, where a coupling is achieved between the sound generating device and a living organism being treated by means of the sound generating device.

The object of the invention is fulfilled by a method for operating a medical robot, which has a robot arm that includes a plurality of members, drives provided for moving the members, and an attaching device, and which has a control device for activating the drives and a sound generating device attached to the attaching device, which is provided to apply sound to a living organism, in particular a high-intensity focused ultrasound, having the following procedural steps:

moving the sound generating device attached to the attaching device into proximity with a surface of the living organism, and under control of the control device, force regulated operation of the drives, so that the robot arm presses the sound generating device against the living organism with a specified force while the sound is being applied to the living organism.

Another aspect of the invention relates to a medical robot for carrying out the method according to the invention. The latter has in particular a robot arm with a plurality of members, drives provided for moving the members, and an attaching device, as well as a sound generating device attached to the attaching device, which is provided to apply sound to a living organism, in particular a high-intensity focused ultrasound, and a control device for activating the drives, which is set up to operate the drives with force regulation, so that the robot arm presses the sound generating device against the living organism with a specified force while the sound is being applied to the living organism.

According to the invention, it is therefore intended that the medical robot to whose attaching device the sound generating device is attached be operated with force regulation, for improved coupling thereof with the living organism being treated by means of the sound generating device. This makes it possible to achieve the result that for example despite a motion of the living organism, caused for example by its breathing, the sound generating device constantly presses against the surface of the living organism, for example its skin, with the specified force.

In order on the one hand to achieve at least adequate coupling between the living organism and the sound generating device, and on the other hand to not press the sound generating device against the living organism too forcefully, the specified force is preferably between 10N and 50N.

The robot may be set up to move the sound generating device into proximity with the living organism automatically with its robot arm.

According to one embodiment of the method according to the invention, the latter includes manual movement of the robot arm, in particular manual guiding, in order to move the sound generating device attached to the attaching device into proximity with the surface of the living organism.

During the manual guiding, gravity-regulated operation of the drives under control of the control device may occur, preferably simultaneously. This enables the robot arm to be guided manually, relatively simply and also reliably.

There may be provision to move the sound generating device by means of the robot along a specified path while simultaneously operating the drives with force regulation, so that the robot arm presses the sound generating device against the living organism with the specified force while the sound generating device is moving along the path. The medical robot according to the invention is intended in particular to treat the living organism for example in conjunction with a tumor treatment by means of the ultrasound generated by the sound generating device. To that end, the focus of the ultrasound should be on the tumor insofar as possible. In addition, there may be provision to apply the ultrasound to the tumor from various sides. Using pictures of the tumor that were taken prior to the treatment, for example using a medical technology device, it is possible to plan the treatment, i.e., the robot may be programmed so that the sound generating device moves in accordance with the plan. Since according to this variant the robot according to the invention is operated with force regulation during the motion, the relatively good coupling between the sound generating device and the living organism is preserved, even during the motion along the path. In particular, there may be provision to operate the robot in one or more spatial directions with force regulation. In the spatial directions in which the robot is not force regulated, it may be operated for example with position regulation, so as for example to traverse a trajectory or path.

According to one embodiment of the robot according to the invention, an imaging medical technology device is also attached to its attaching device. According to one variant of the method according to the invention, the following procedural steps are provided in addition:

creation of at least one image, or of an image data record, using an imaging medical technology device attached to the attaching device, while the sound is being applied to the living organism, evaluation of the image or image data record, and depending on the evaluated image or image data record, adjusting a focus of the sound generating device or moving the robot arm so that the focus of the sound generating device falls on a tissue of the living organism which is to be treated.

On the basis of the imaging medical technology device, which is in particular an ultrasound device, it is accordingly possible, during the treatment with the sound generating device, to create an image or images of the living organism, in particular of its tissue that is being treated. This image may be displayed for example on a viewing device, so that the focus of the sound generating device can be readjusted manually if necessary. Preferably, however, the image or image data record is evaluated automatically, in order to readjust the focus of the sound generating device automatically for example, or to move the latter using the robot arm.

According to another variant of the method according to the invention, it also includes the following:

operation of at least one additional medical robot, which has a robot arm that includes a plurality of members, drives provided to move the members, and an attaching device, and which has a control device to activate the drives of the second robot, and an additional sound generating device attached to the attaching device of the additional robot, which is provided to apply sound to the living organism, in particular a high intensity focused ultrasound, moving the additional sound generating device attached to the attaching device of the additional robot into proximity with the surface of the living organism, and under control of the control device of the additional robot, force regulated operation of the drive of the additional robot, so that the robot arm of the additional robot presses the additional sound generating device against the living organism with a specified force while the sound is being applied to the living organism.

Thus an additional aspect of the invention relates to a medical work station which includes essentially a plurality of medical robots according to the invention, so that the living organism can be treated simultaneously with at least two sound generating devices, each of which is pressed against the living organism by the robot arm with force regulation. This makes it possible to shorten the duration of the treatment.

The method according to the invention is intended in particular to treat the living organism using high intensity focused ultrasound (HIFU). HIFU is an option for heating tissue selectively with ultrasound waves, and thus destroying it.

The sound generating device, in particular an ultrasound transducer, is used, which makes it possible to focus the generated sound cone in such a way that the energy becomes so high at a desired location that the tissue located there is heated. The heating, for example to 60 to 80° C., preferably takes place in a relatively limited focal zone. This results in necrosis of the tissue.

In order to introduce the ultrasound into the living organism as well as possible, there should be no air present between the sound generating device, for example the transducer, and the living organism, since the sound is reflected at least partially, if not indeed completely, at the air boundary.

Depending on the embodiment, the invention provides a robot system to whose flange or attaching device a sound generating device, designed in particular as a HIFU transducer, is attached, and which preferably presses the transducer constantly onto the surface of the skin of the living organism during the treatment, by means of force regulation. This system can have the following benefits:

It makes extracorporeal HIFU without water basins possible, enabling the treatment to be carried out more flexibly and also non-invasively.

Conformal treatment with relatively freely selectable and combinable irradiation directions can result, whereby it may be possible to improve adjustment of the dosage to the tumor in the present living organism or to the present treatment.

Adaptive treatment with compensation for movements of the tumor by means of force sensing and/or online imaging becomes possible, whereby adaptation of the treatment to the present morphological situation is enabled.

The possibility of multi-transducer treatment through the use of a plurality of robot arms may be provided, whereby the treatment may be shortened.

The medical robot according to the invention is equipped with force regulating properties. It may preferably be possible to assign parameters to the force to be regulated.

In addition, gravity regulation may be provided for the manual guidance. The robot according to the invention can thereby be prepositioned for example at the approximate target position, using manual guidance.

On the basis of the method according to the invention, it is possible to move the sound generating device, in particular in the form of a transducer, on the surface of the living organism during the treatment, without changing the pressing force of the transducer. It is also possible for the focus of the ultrasound to remain constantly in the tumor during the motion.

Through the use of the robot according to the invention, it is possible to plan much more flexibly in the planning step, since the directions of irradiation are more flexible, in contrast to conventional systems. Possible obstructions between the tissue to be treated and the sound generating device, for example bone or air, may be circumvented relatively easily by varying the direction of irradiation.

Possibly using a tracking system (robot and living organism are tracked), the robot according to the invention is able to move to the planned target position relatively precisely.

An adaptive treatment can be realized. The robot according to the invention can be employed in a complete system, as part of a treatment sequence. For example, using online imaging with an imaging medical technology device, in particular an ultrasound transducer, which may also be attached to the attaching device and is fixed in relation to the sound generating device, movements of the tissue to be treated can be recognized during the treatment and compensated for if necessary. Changes between the time the planning images were recorded and the treatment can be recognized and compensated for if necessary. The position of the tissue to be treated can change due to different degrees of filling for example of hollow organs such as the bladder. In addition, breathing movements on the surface of the skin may be recognized using force sensors, and compensated for with the aid of force regulation.

Multi-transducer treatment may possibly be used. Through the possible use of a second or even a third robot arm, even better convergence may be achieved; that is, the dosage may be amplified by superimposing a plurality of foci, or the treatment may be greatly shortened by a plurality of independent foci.

Figure 2:
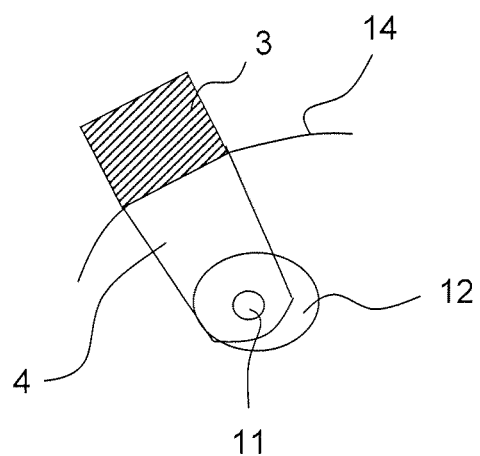

Examples of exemplary embodiments of the invention are depicted in the accompanying schematic drawing. The figures show the following:

FIG. 1 a medical workstation,

FIG. 2 a device for generating high intensity focused ultrasound, and

Figure 3:
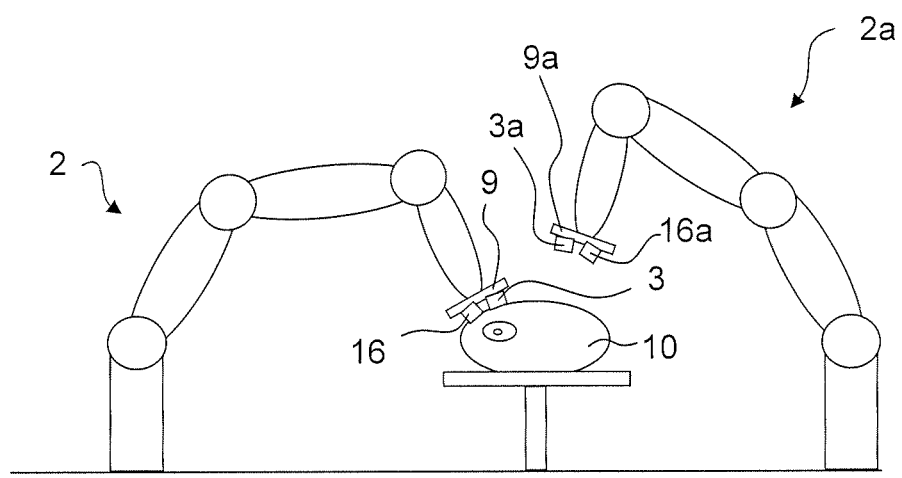

FIG. 3 an additional medical workstation,

FIG. 1 shows a medical workstation 1 having a medical robot 2, to which is attached a sound generating device 3, which is set up to generate a so-called high intensity focused ultrasound, whose sound cone 4 is shown in FIG. 2.

Robot 2, which is designed in particular as a lightweight robot, has in the case of the present exemplary embodiment a robot arm 5 and a control device 6 that controls the motion of robot arm 5. Robot arm 5 has a plurality of members 7, which are connected via joints 8. The members 7, which are movable by means of drives 15, can thus be moved in reference to axes of motion. The drives 15 are in particular regulated drives, for example regulated electric drives, which are activated by control device 6. Robot arm 5 may be moved for example in reference to six or even more degrees of freedom.

Robot arm 5 has an attaching device 9, for example in the form of a flange. Sound generating device 3 is attached to attaching device 9. This is provided in the case of the present exemplary embodiment so that a living organism 10 is treated thereby. Living organism 10 lies for example on a patient table 13.

In particular, sound generating device 3 is provided so that a tumor 11 for example of the liver 12 of living organism 10 is treated by means of the high intensity focused ultrasound generated by it. In order for the high intensity focused ultrasound generated by sound generating device 3 to be able to reach and heat tumor 11, sound generating device 3 is coupled during the treatment with the surface of living organism 10, in particular with the latter's skin 14.

In the case of the present exemplary embodiment, it is provided that during the treatment of living organism 10, robot 2, in particular robot arm 5, controlled by control device 6, automatically presses sound generating device 3 against living organism 10 with a previously set pressure, in order to obtain at least a satisfactory coupling of sound generating device 3 with the skin 14 of living organism 10.

So that robot arm 5 presses sound generating device 3 against living organism 10 with the set force, in the case of the present exemplary embodiment a computer program is running on control device 6 which activates robot arm 5, or the drives 15 of robot arm 5, in such a way that they press attaching device 9 and hence sound generating device 3 against living organism 10 under force regulation with the specified force. The specified force is for example 10N to 50N. This results in at least a satisfactory coupling between sound generating device 3 and living organism 10 during the treatment, even if living organism 10 moves relative to sound generating device 3, for example due to breathing.

Robot 2 may be designed so that it moves sound generating device 3 into proximity with living organism 10 automatically by means of its robot arm 5. Robot 2 may also be designed so that it is moved into proximity with living organism 10 manually, in particular that it is guided manually. This may be realized for example by a person not shown in further detail, for example a doctor treating living organism 10, moving robot arm 5 into proximity with living organism 10 by pulling and/or pushing it. In particular, in this case robot 2 may include gravity regulation. This may be realized for example by a computer program running on control device 6, which activates drives 15 during the manual guiding in such a way that they support the manual guiding.

In the case of the present exemplary embodiment, prior to the treatment of living organism 10, at least one image or image data record of tumor 11 is created by means of an imaging medical technology device, for example by means of an ultrasound device, an x-ray device, a computer tomography device or a magnet resonance device, and the treatment is planned on the basis of this image or image data record. During the treatment, it may be provided that the ultrasound of sound generating device 3 is applied to tumor 11 from various directions. To that end, robot 2 may be set up to move robot arm 5 automatically on the basis of the plan. During the motion, robot 2 is under force regulation, so that robot arm 5 presses sound generating device 3 against living organism 10 with the specified force. A manual motion may also be provided during the treatment, it possibly being provided that that robot arm 5 presses sound generating device 3 against living organism 10 with the specified force due to the force regulation.

In the case of the present exemplary embodiment, it may also be provided that in addition to sound generating device 3 an imaging medical technology device is attached to attaching device 9 of robot arm 5. This device, which is in particular an ultrasound device 16, is attached to attaching device 9 in particular in a known relationship to sound generating device 3. By means of imaging medical technology device or ultrasound device 16, it is possible for example during the treatment for at least one image of tumor 11 to be created, in order for example to track robot arm 5 automatically in such a way that a focus of the ultrasound generated by sound generating device 3 is in tumor 11, insofar as possible. It is also possible that the focus of sound generating device 3 is automatically readjusted by means of the imaging medical technology device. To that end, for example, sound generating device 3 and ultrasound device 16 are connected to control device 6 in a manner not shown. It is also possible that the image created by means of the imaging medical technology device is displayed on a viewing device, not depicted in greater detail, so that possibly for example the doctor treating living organism 10 can readjust the focus of sound generating device 3.

FIG. 3 shows another medical work station, which includes in addition to robot 2 at least one additional robot 2a. Attached to attaching device 9a of the latter's robot arm is likewise a sound generating device 3a, which is set up to generate a high intensity focused ultrasound in order to treat living organism 10. Robot 2a is likewise force regulated, so that its sound generating device 3a presses against living organism 10 with a specified force.

An imaging medical technology device, for example an ultrasound device 16a, may also be attached to attaching device 9a of additional robot 2a. The two robots 2, 2a can be designed essentially identically. Living organism 10 can be treated simultaneously, using the two robots 2, 2a.

The invention claimed is:

1. A method for operating a medical robot that includes a robot arm comprising a plurality of links and drives configured for moving the links, a control device for activating the drives, and a sound generating device coupled to the robot arm and configured to apply high-intensity focused ultrasound to a living organism, the method comprising:

moving the robot arm so as to position the sound generating device on a surface of the living organism;

moving the robot arm so that the sound generating device moves along a specified path while simultaneously applying high-intensity focused ultrasound to treat tissue with the high-intensity focused ultrasound;

simultaneously with moving the robot arm along the specified path, operating the drives of the robot arm utilizing force control such that the sound generating device is pressed against the living organism with a specified constant value force while the sound generating device is moving along the specified path;

creating at least one image while the high-intensity focused ultrasound is being applied to the living organism;

evaluating the at least one image; and based on the evaluating step, adjusting a focus of ultrasound emanating from the sound generating device so that the focus of the sound generating device falls on a tissue of the living organism which is to be treated.

2. The method according to claim 1, wherein the specified constant value force is a force value selected from the range of 10 N to 50 N.

3. The method according to claim 1, wherein moving the robot arm further comprises manually moving the robot arm, the method further comprising:

using the control device to simultaneously operate the drives under gravity regulation during manual movement of the sound generating device.

4. The method according to claim 1, further comprising moving the robot arm so that the focus of the sound generating device falls on a tissue of the living organism which is to be treated.

5. The method according to claim 1, wherein creating at least one image comprises creating an image data record.

6. The method according to claim 1, wherein evaluating the at least one image further comprises automatic evaluation of the at least one image, and adjusting the focus of the sound generating device comprises automatic adjustment of the focus of the sound generating device.

7. The method according to claim 1, wherein the specified constant value force is dependent upon the specified path.

8. The method according to claim 1, further comprising:

operating at least one additional medical robot having a robot arm with a plurality of links and drives configured for moving the links, a control device for activating the drives, and a sound generating device coupled to the robot arm and configured to apply sound to a living organism;

moving the additional robot arm so as to position the additional sound generating device on a surface of the living organism;

moving the additional robot arm so that the additional sound generating device moves along a specified path; and using the control device of the additional robot to operate the drives of the additional robot arm utilizing force control so as to simultaneously press the additional sound generating device against the living organism with a specified constant value force while the sound generating device is moving along the specified path.

9. The method according to claim 8, wherein the specified constant value force associated with the additional robot arm is dependent upon the specified path.

10. A medical work station, comprising:

a first medical robot, the first medical robot comprising:

a robot arm having a plurality of links, drives configured for moving the links, and an attaching device;

a sound generating device attached to the attaching device and configured to apply high-intensity focused ultrasound to a living organism; and a control device for activating the drives, the control device operating the drives such that the robot arm moves the sound generating device along a specified path and simultaneously maintains the sound generating device pressed against the living organism with a specified constant value force while the sound generating device is moved along the specified path and simultaneously applies high-intensity focused ultrasound to treat tissue with the high-intensity focused ultrasound;

wherein the specified constant value force is dependent upon the specified path.

11. The medical work station according to claim 10, further comprising:

a second medical robot, the second medical robot comprising:

a second robot arm having a plurality of links, drives configured for moving the links, and an attaching device;

a second sound generating device attached to the attaching device and configured to apply sound to the living organism; and a second control device for activating the drives of the second robot arm, the second control device operating the drives such that the second robot arm maintains the second sound generating device pressed against the living organism with a specified constant force while the second sound generating device is moved along a specified path.

12. The medical work station of claim 11, wherein the specified constant force maintained by the second robot arm is dependent upon the specified path.

13. The medical work station according to claim 10, further comprising:

an imaging device configured to obtain an image of the living organism while the high-intensity focused ultrasound is being applied to the living organism;

the control device configured to adjust a focus of the high-intensity focused ultrasound emanating from the sound generating device based on the image obtained with the imaging device, so that the focus of the sound generating device falls on a tissue of the living organism which is to be treated.

14. The medical work station according to claim 13, wherein the control device is further configured to move the robot arm based on the image obtained with the imaging device so that the focus of the sound generating device falls on a tissue of the living organism which is to be treated.

* * * * *